(12) United States Patent
Moszner et al.

(10) Patent No.: US 6,284,898 B1
(45) Date of Patent: Sep. 4, 2001

(54) HYDROLYSABLE AND POLYMERIZABLE OXETANE SILANES

(75) Inventors: Norbert Moszner, Eschen (LI); Thomas Voelkel, Lindau (DE); Sabine Stein, Nenzing (AT); Volker Rheinberger, Vaduz (LI)

(73) Assignee: Ivoclar AG (LI)

( * ) Notice: Subject to any disclaimer, the term of this patent is extended or adjusted under 35 U.S.C. 154(b) by 0 days.

(21) Appl. No.: 09/591,358

(22) Filed: Jun. 9, 2000

Related U.S. Application Data

(62) Division of application No. 09/047,659, filed on Mar. 25, 1998, now Pat. No. 6,096,903.
(60) Provisional application No. 60/052,563, filed on Jul. 15, 1997.

(30) Foreign Application Priority Data

Mar. 25, 1997 (DE) ............................................. 197 14 324

(51) Int. Cl.[7] ...................... C07D 305/04; C08G 65/18; C08G 77/14

(52) U.S. Cl. .......................... 549/214; 549/510; 549/511; 522/168; 522/172

(58) Field of Search ..................................... 549/214, 510, 549/511; 522/168, 172

(56) References Cited

U.S. PATENT DOCUMENTS 5,463,084   10/1995   Crivello et al. ...................... 549/214

FOREIGN PATENT DOCUMENTS

4133494A1   9/1991   (DE) .

*Primary Examiner*—Ba K. Trinh
(74) *Attorney, Agent, or Firm*—Nixon Peabody LLP

(57) ABSTRACT

Polymerizable and hydrolysable oxetane silanes and in particular silicic acid condensates which can be prepared therefrom are described, which exhibit only a low volume shrinkage on polymerization and produce polymers with high mechanical strength and therefore can be used above all as dental material or constituent thereof.

5 Claims, No Drawings

HYDROLYSABLE AND POLYMERIZABLE OXETANE SILANES

This application is a divisional of Ser. No. 09/047,659 filed Mar. 25, 1998, now U.S. Pat. No. 6,096,903 which claims the priority benefit of provisional application no. 60/052,563, dated Jul. 15, 1997.

The invention relates to hydrolysable and polymerizable oxetane silanes, a process for the preparation thereof, silicic acid condensates, polymers and compositions prepared therefrom and the use of all these materials inter alia for the preparation of macromolecular compositions by polymerization and for the preparation of composite materials, adhesives, coatings and in particular dental materials.

Hydrolysable silanes, which contain polymerizable organic radicals, are used in the preparation of coatings, particulate fillers, adhesive compositions and monolithic moulded articles and in the surface modification of reinforcing substances. The silanes are hydrolytically condensed and polymerized thermally, photochemically or by redox initiation, i.e. cured, alone, mixed with other silanes or in the presence of other metal alkoxides.

Of particular interest in connection with the preparation of organic-inorganic composite materials are above all organically modified silanes with polymerizable organic groups, such as vinyl, (meth)acrylic, allyl or styryl groups, since they permit the simultaneous or consecutive formation both of an inorganic and of an organic network and therefore of composite materials with customized properties (cf H. Schmidt, Mat. Res. Soc. Symp. Proc. Vol. 32 (1984), 327–335; H. Schmidt, H. Wolter, J. Non-Cryst. Solids 121 (1990) 428–435). The polymerizable silanes are as a rule in the first step hydrolytically condensed in solution. After the addition of thermal initiator or photoinitiator and removal of the solvent, nanoparticulate resins then form which are shaped and then polymerized and thus cured.

A major disadvantage of these materials, however, is that the development of the organic network which takes place on polymerization is mostly accompanied by a considerable volume contraction which may result in deformation of the moulded articles, reduction in substrate adhesion, layer separation, development of voids or development of material stresses. A reduced volume contraction takes place with silanes which bear ring-opening groups. In this connection, EP-B-0 358 011 describes scratch-resistant materials inter alia based on 3-glycidyloxypropyl silanes, EP-B-0 486 469 describes organic-inorganic hybrid polymers of 3-glycidyloxypropyl silanes and DE-C-41 33 494 describes dental resin compositions in which e.g. silanes with ring-opening spiroortho ester groups are used. It proves to be disadvantageous, however, that epoxide silanes are toxicologically unacceptable and cationically polymerize sufficiently quickly at elevated temperatures only. Furthermore, spiroortho ester silanes exhibit only a low stability and their cationic ring-opening polymerization is generally accompanied by the formation of lactone.

Furthermore, the following silicon-containing oxetane derivatives are also known:

1. Silicon-containing oxetanes which are obtainable e.g. by hydrosilylation of 3-allyloxymethyl-3-ethyl-oxetane with 1,1,3,3-tetramethyldisiloxane (cf J. V. Crivello et al., J. Macromol. Sci.-Pure Appl. Chem. A30 (1993), 173–187):

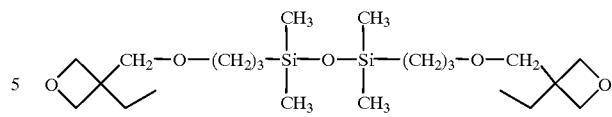

2. 3-(trimethylsiloxy)-oxetanes which can be synthesized by Paterno-Büchi reaction (cf T. Bach, Tetrahedron Lett. 32 (1991), 7037–8):

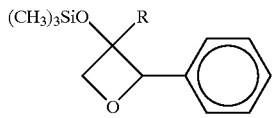

(R: Phenyl, tert-butyl, tert-butyl-s)

3. 3-Alkyl-3-(triorganosiloxymethyl)-oxetanes or 3-alkyl-3-(triorganosilylmethyl)-oxetanes (cf DE-A-195 06 222):

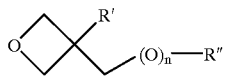

(R' = H, $C_{1-10}$ alkyl; n: = 1; R'': Si(alkyl)$_3$, Si(aryl)$_3$ or Si(oxyalkyl)$_3$)

4. 3,3-bis(triorganosiloxymethyl)-oxetanes which can be obtained by reacting 3,3-bis(hydroxymethyl)-oxetanes with appropriate triorganoaminosiloxanes $R_3SiNH_2$ (cf Chem. Abstr. 76 (192) 14701k):

(R: alkyl, aryl or halogen alkyl)

It is the object of the invention to provide hydrolysable and polymerizable oxetane silanes from which, alone or together with other hydrolytically condensable and polymerizable components, stable compositions can be prepared which polymerize with only low shrinkage and at high speed at room temperature, and which are suitable as composite or coating material, adhesive or adhesion promoter or for the preparation of fillers or materials for medical or dental purposes. These silanes are to be able to be covalently incorporated into organic-inorganic composite materials and be synthetically obtainable so that the distance between silicon and the polymerizable groups can be varied.

This object is achieved according to the invention by the hydrolysable and polymerizable oxetane silanes according to Claims 1 to 3. The invention further relates to the silicic acid condensates according to Claim 4, the polymerizates according to Claim 5, the compositions according to Claims 6 and 7 and the use according to Claim 8.

The hydrolysable and polymerizable oxetane silanes according to the invention and the stereoisomers thereof correspond to the general formula (I):

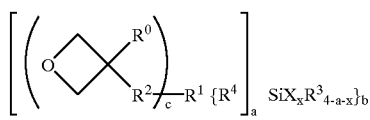

(I)

in which the variables $R^0$, $R^1$, $R^2$, $R^3$, $R^4$, $R^5$, $R^6$, X, Y, a, b, c, and x, unless otherwise stated, independently of one another have the following meanings:

$R^0$=hydrogen or substituted or unsubstituted $C_1$ to $C_{10}$ alkyl;

$R^1$=missing or represents substituted or unsubstituted $C_1$ to $C_{18}$ alkylene, $C_6$ to $C_{18}$ arylene, $C_7$ to $C_{18}$ alkylenearylene or arylenealkylene, these radicals being able to be interrupted by at least one group selected from ether, thioether, ester, carbonyl, amide and urethane groups;

$R^2$=missing or represents substituted or unsubstituted $C_1$ to $C_{18}$ alkylene, $C_6$ to $C_{18}$ arylene, $C_7$ to $C_{18}$ alkylenearylene or $C_7$ to $C_{18}$ arylenealkylene, these radicals being able to be interrupted by at least one group selected from ether, thioether, ester, thioester, carbonyl, amide and urethane groups or being able to bear these in the terminal position;

$R^3$=missing or represents substituted or unsubstituted $C_1$ to $C_{18}$ alkyl, $C_2$ to $C_{18}$ alkenyl, $C_6$ to $C_{18}$ aryl, $C_7$ to $C_{18}$ alkylaryl or $C_7$ to $C_{18}$ arylalkyl, these radicals being able to be interrupted by at least one group selected from ether, thioether, ester, carbonyl, amide and urethane groups;

$R^4$=missing or represents substituted or unsubstituted —$CHR^6$—$CHR^6$—, —$CHR^6$—$CHR^6$—S—$R^5$, —S—$R^5$—, Y—CO—NH—$R^5$— or —CO—O—$R^5$—;

$R^5$=substituted or unsubstituted $C_1$ to $C_{18}$ alkylene, $C_6$ to $C_{18}$ arylene, $C_6$ to $C_{18}$ alkylenearylene or $C_6$ to $C_{18}$ arylenealkylene, these radicals being able to be interrupted by at least one group selected from ether, thioether, ester, carbonyl, amide and urethane groups;

$R^6$=hydrogen or substituted or unsubstituted $C_1$ to $C_{18}$ alkyl or $C_6$ to $C_{10}$ aryl;

X=a hydrolysable group, namely halogen, hydroxy, alkoxy or acyloxy;

Y=O or S;

a=1, 2 or 3;

b=1, 2 or 3;

c=1 to 6; and x=1, 2 or 3;

and with the proviso that (i) a+x=2, 3 or 4 and (ii) a and/or b=1.

However, the above formula covers only those compounds which are compatible with the valency theory.

The silanes according to the invention are usually present as stereoisomer mixtures and in particular as racemates.

The ether, thioether, ester, thioester, carbonyl, amide and urethane groups which are possibly present in the radicals are defined by the following formulae: —O—, —S—, —CO—O—, —O—CO—, —CO—S—, —S—CO—, —CS—O—, —O—CS—, —CO—, —CO—NH—, —NH—CO—, —O—CO—NH— and —NH—CO—O—.

The non-aromatic radicals or non-aromatic parts of the radicals possible in formula (I) can be straight-chained, branched or cyclic.

Alkyl radicals have preferably 1 to 8 and particularly preferably 1 to 4 carbon atoms. Particular examples of possible alkyl radicals are methyl, ethyl, n- and iso-propyl, sec- and tert-butyl, n-pentyl, cyclohexyl, 2-ethylhexyl and octadecyl.

Alkenyl radicals have preferably 2 to 10 and particularly preferably 2 to 6 carbon atoms. Particular examples of possible alkenyl radicals are vinyl, allyl and iso-butenyl.

Preferred examples of possible aryl radicals are phenyl, biphenyl and naphthyl.

Alkoxy radicals preferably have 1 to 6 carbon atoms. Particular examples of possible alkoxy radicals are methoxy, ethoxy, n-propoxyl iso-propoxy and tert-butoxy.

Acyloxy radicals preferably have 2 to 5 carbon atoms. Particular examples are acetyloxy and propionyloxy.

Preferred alkylene radicals are derived from the above preferred alkyl radicals and preferred arylene radicals are derived from the above preferred aryl radicals.

Preferred radicals consisting of a combination of non-aromatic and aromatic parts, such as alkylaryl, arylalkyl, alkylenearylene and arylenealkylene radicals, are derived from the above preferred alkyl and aryl radicals. Particular examples thereof are benzyl, 2-phenylethyl and tolyl.

The mentioned substituted R radicals bear one or more simple substituents. Examples of these substituents are methyl, ethyl, phenyl, benzyl, hydroxymethyl, hydroxyethyl, methoxy, ethoxy, chloro, bromo, hydroxy, mercapto, isocyanato, vinyloxy, acryloxy, methacryloxy, allyl, styryl, epoxy, carboxyl, $SO_3H$, $PO_3H_2$ or $PO_4H_2$.

For a, b, c or $x \geq 2$, the radicals X and the individual R radicals can in each case have the same or a different meaning.

Moreover, preferred definitions exist for the above-stated variables of formula (I) which, unless otherwise stated, can be chosen independently of one another and are as follows:

$R^0$=hydrogen or $C_1$ to $C_5$ alkyl;

$R^1$=$C_1$ to $C_8$ alkylene, these radicals being able to be interrupted by at least one group selected from ether, thioether, ester and urethane groups;

$R^2$=missing or represents $C_1$ to $C_8$ alkylene, these radicals being able to be interrupted by at least one group selected from ether, thioether, ester, thioester, carbonyl, amide and urethane groups or being able to bear these in the terminal position;

$R^3$=missing or represents methyl, ethyl or phenyl;

$R^4$=missing or represents —$CHR^6$—$CHR^6$—, —S—$R^5$—, —Y—CO—NH—$R^5$— or —CO—O—$R^5$—;

$R^5$=$C_1$ to $C_8$ alkylene, these radicals being able to be interrupted by at least one group selected from ether, thioether, ester, carbonyl, amide and urethane groups;

$R^6$=hydrogen or $C_1$ to $C_5$ alkyl;

X=methoxy, ethoxy or chloro;

Y=O or S;

a=1;

b=1;

c=1 to 6;

x=2 or 3; and/or a+x 3.

The individual R radicals can in turn bear simple substituents.

Preferred compounds are accordingly those in which at least one of the variables of formula (I) has the above-described preferred definition.

Furthermore, those oxetane silanes of formula (I) are preferred in which the indices a, b and/or c have the value 1, and examples thereof are the silanes according to the general formulae (II), (III), (IV) and (V) below.

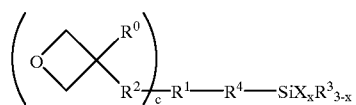
(Formula II)

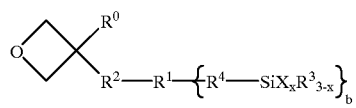
(Formula III)

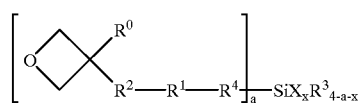
(Formula IV)

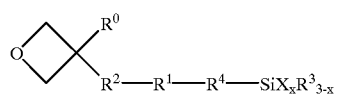
(Formula V)

Particular examples of preferred oxetane silanes according to the invention of formula (I) are given below:

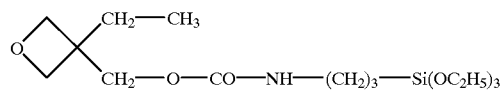

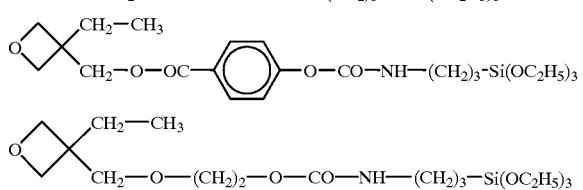

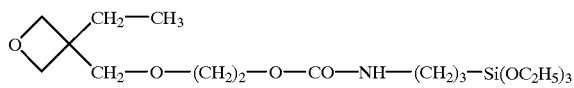

The preparation of the oxetane silanes (I) according to the invention is possible in particular via a large number of conventional addition or condensation reactions which are carried out according to the methods customary for these reactions. Processes which can be used for preparing the silanes according to the invention are described e.g. in W. Noll, Chemie und Technologie der Silicone, 2nd edition, Verlag Chemie, Weinheim 1968, in particular p. 22 et seq., and in the review by R. C. Mehrotra in J. Non-Crystalline Solids 100, (1988) 1–15 and the literature quoted in this article.

In a first variant, e.g. 3-ethyl-3-hydroxymethyl oxetane (1) can be added to an isocyanate group-containing silane:

Isocyanate addition

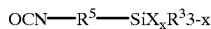

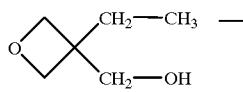

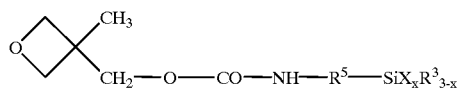

Concrete example

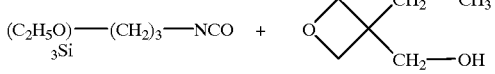

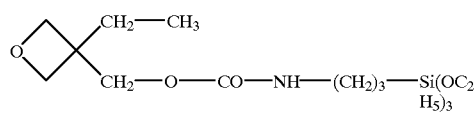

Furthermore, starting from 3-acryloyloxymethyl-3-ethyloxetane (2), e.g. the thiol-ene addition with mercaptosilanes is possible:

Thiol-ene addition

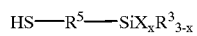

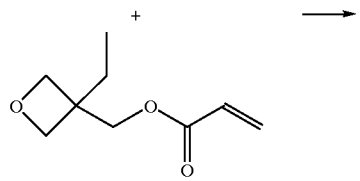

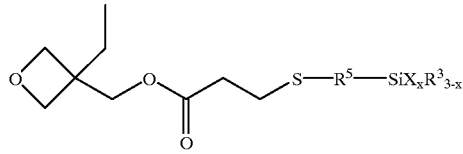

Concrete example

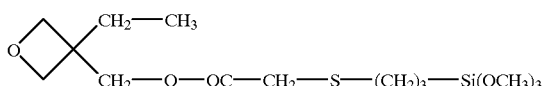

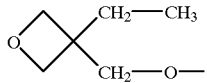

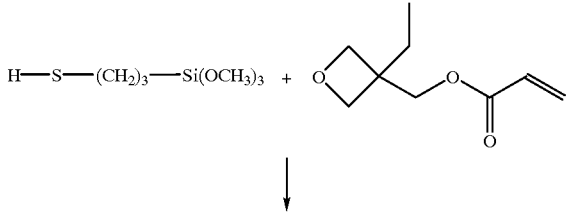

Moreover, the semi-ester of fumaric acid and 3-ethyl-3-hyroxymethyl-oxetane can be added to an epoxide silane:

Epoxide addition

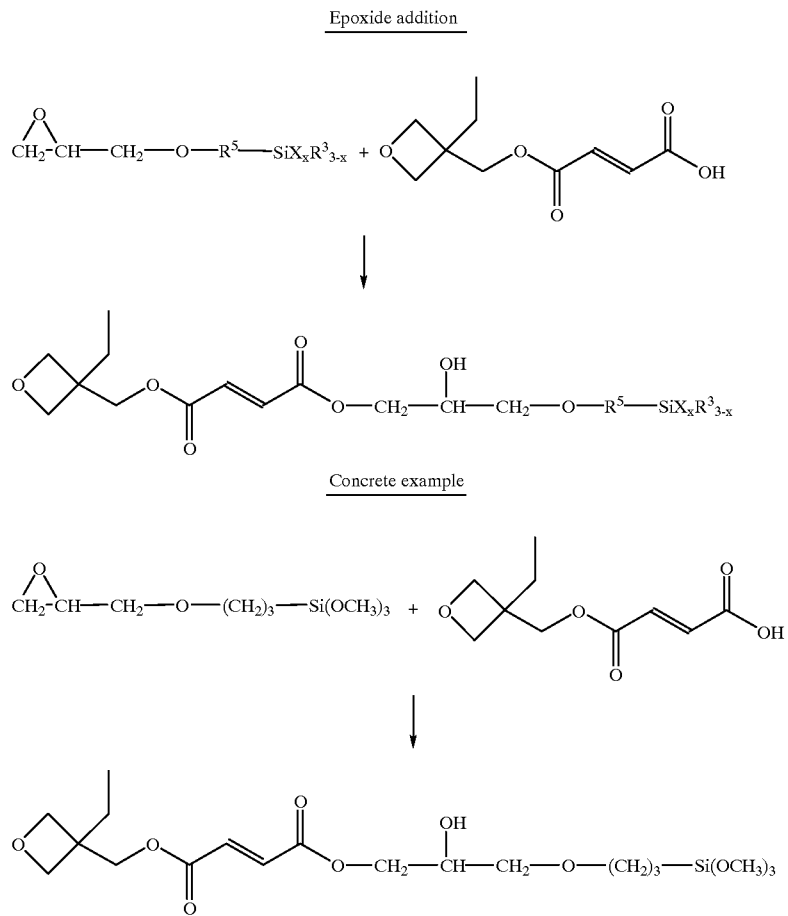

Concrete example

The silane obtained can be reacted further with an isocyanate group-containing silane, so that oxetane silanes with two silyl groups are obtained:

Combination of isocyanate and epoxide additions

Silanes with several oxetane radicals are accessible via addition reactions. Thus, e.g. by reacting (1) with tetracarboxylic acid dianhydrides, such as pyromellitic acid anhydride, 1,2,3,4-butanetetracarboxylic acid dianhydride or tetrahydrofuran-2,3,4,5-tetracarboxylic acid dianhydride, an adduct can be obtained which is further reacted with 1 or 2 mol of an epoxide or isocyanatosilane.

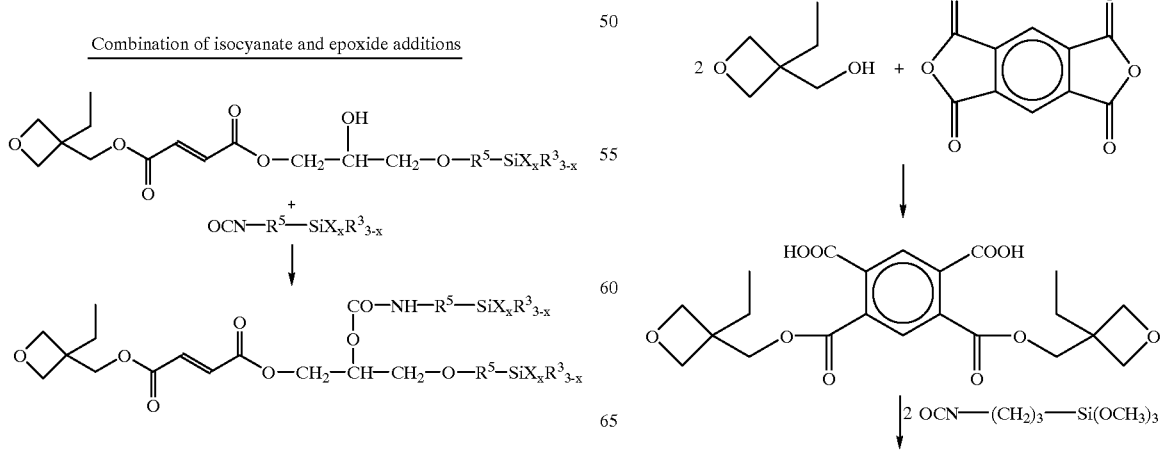

-continued

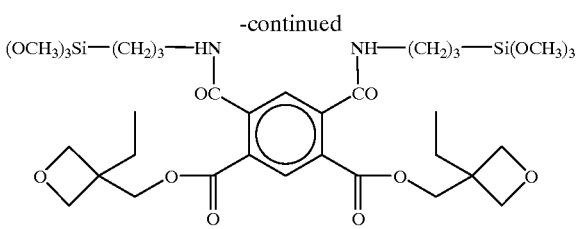

The silanes (I) according to the invention are polymerizable via the oxetane groups and hydrolysable via the radicals X. The polymerization of the oxetane groups leads to the formation of an organic network, whereas the hydrolysable groups produce an inorganic polysiloxane network through polycondensation.

The oxetane silanes according to the invention are substances of high reactivity which on hydrolysis form polymerizable silicic acid condensates which can be polymerized in the presence of usual cationic initiators or photoinitiators at room temperature or under irradiation with light of the visible or UV range to form mechanically stable layers, moulded articles or fillers.

The number of hydrolysable groups, polymerizable groups and further functional groups can be varied by suitable selection of the starting materials used in the preparation of the oxetane silanes. Depending on the type and number of the hydrolysable groups, e.g. alkoxy groups, and on the number of oxetane groups, the condensation of the oxetane silanes and the polymerization of the obtained condensates therefore results in materials with properties which range from silicone rubber-like to glass-like. In comparison with radically polymerizable silanes, no inhibition layer forms on polymerization of the oxetane silanes according to the invention, which is very advantageous especially in the preparation of coatings.

The development of a three-dimensional, organic network is possible when at least two oxetane radicals are present, the mechanical properties, such as e.g. strength and flexibility, and the physico-chemical properties, e.g. adhesiveness, water absorption and refractive index, of the obtained silicic acid condensates being variable and optimally adaptable to the requirements of the respective case of application via the distance between the Si atom and the oxetane radical, i.e. via the length of the spacer group, and by incorporation of further functional groups. Aliphatic groups result in products which are rather flexible, and aromatic groups result in products which are rather rigid.

Furthermore, the crosslinking density, which then likewise influences the properties and possible applications of the corresponding silicic acid condensates, can be set by means of the number of polymerizable oxetane groups. Moreover, if the oxetane silanes according to the invention also contain ionically crosslinkable groups such as e.g. (meth)acrylate, styryl or allyl, then a further increase in crosslinking density can be achieved simultaneously or consecutively, i.e. as a 2-stage process, by their radical polymerization.

The oxetane silanes according to the invention and their silicic acid condensates possess only a low volatility, with the result that they can be processed in an easy and largely harmless manner. In view of the above-stated variation possibilities of the condensable and polymerizable radicals of the oxetane silanes according to the invention, silicic acid condensates which can be prepared therefrom can be provided as resins or fillers for very different areas of application.

The silanes (I) are stable compounds which can be processed either alone or together with other hydrolysable, condensable and/or polymerizable components to form the silicic acid condensates according to the invention.

In addition to the silanes of formula (I), other hydrolytically condensable compounds of silicon, aluminium, titanium, zirconium or phosphorus can be used in the preparation of the silicic acid condensates according to the invention, which are then also referred to as silicic acid (hetero)condensates. These compounds can be used either as such or in already precondensed form. It is preferred that at least 20 mol. %, particularly preferably at least 80 mol. %, based on monomeric compounds, of hydrolysable silicon compounds are used for the preparation of the silicic acid (hetero)condensates according to the invention. It is also preferred that at least 10 mol. %, in particular 40 to 100 mol. %, in each case based on monomeric compounds, of oxetane silanes according to the invention are used for the preparation of the silicic acid (hetero)condensates.

Preferably at least one silane of the general formula (VI) is used as other hydrolytically condensable compounds:

in which $R^7$, $Z'$, $R^8$, $X'$, k and m, unless otherwise stated, independently of one another have the following meanings:

$R^7 = C_1$ to $C_8$ alkyl, $C_2$ to $C_{12}$ alkenyl or $C_6$ to $C_{14}$ aryl;

$R^8 = C_1$ to $C_8$ alkylene, $C_2$ to $C_{12}$ alkenylene or $C_6$ to $C_{14}$ arylene;

$X'$=hydrogen, halogen or $C_1$ to $C_8$ alkoxy;

$Z'$=mercapto, glycidyl, acrylic, methacrylic, vinyl, allyl or vinyl ether group;

k=0, 1, 2 or 3;

m=0, 1, 2 or 3; and k+m=1, 2 or 3.

Such silanes are described e.g. in DE-C-34 07 087, and particular examples of hydrolytically condensable silanes of general formula (VI) are:

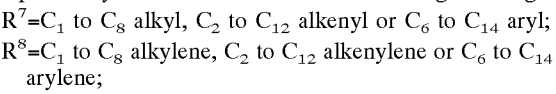

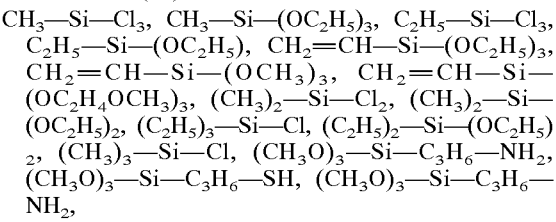

Furthermore, at least one zirconium, titanium or aluminium compound of the formulae

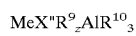

can be used as other preferred hydrolytically condensable compounds, in which Me, $R^9$, $R^{10}$, $X''$, y and z independently of one another have the following meanings:

Me=Zr or Ti;

$R^9$=hydrogen, substituted or unsubstituted $C_1$ to $C_{12}$ alkyl, $C_7$ to $C_{15}$ alkylaryl or $C_6$ to $C_{14}$ aryl;

$R^{10}$=halogen, OH, $C_1$ to $C_8$ alkoxy;

X"=halogen, OH, C, to $C_8$ alkoxy;
y=1 to 4, in particular 2 to 4;
z=1 to 3, in particular 0 to 2.

Preferred examples of zirconium and titanium compounds which can be used are $ZrCl_4$, $Zr(OC_2H_5)_4$, $Zr(OC_3H_7)_4$, $Zr(OC_4H_9)_4$, $ZrOCl_2$, $TiCl_4$, $Ti(OC_2H_5)_4$, $Ti(OC_3H_7)_4$ and $Ti(OC_4H_9)_4$. Preferred examples of aluminium compounds which can be used are $Al(OCH_3)_3$, $Al(OC_2H_5)_3$, $Al(OC_3H_7)_3$, $Al(OC_4H_9)_3$ and $AlCl_3$.

Complexed Zr, Ti and Al compounds can also be used, in which inter alia acids or β-dicarbonyl compounds can act as complexing agents.

Other hydrolysable compounds which can be used for preparing the silicic acid (hetero)condensates are e.g. boron trihalides, tin tetrahalides, tin tetraalkoxides and vanadyl compounds.

The silicic acid condensates according to the invention of the silanes (I) are obtained by hydrolysis of the hydrolysable groups X present, e.g. alkoxy groups, and by subsequent condensation, which results in the formation of an inorganic network of Si—O—Si units. The hydrolysis and condensation usually take place in basic or acidic medium, a linking of C=C double bonds which are contained in the silanes used being generally undesired.

The silicic acid condensates according to the invention can also be present in incompletely hydrolysed and condensed form. In such cases, they are referred to as so-called precondensates.

The customary procedure in the preparation of the silicic acid (hetero)condensates according to the invention is that the silanes (I), optionally dissolved in a solvent, are reacted at room temperature or with slight cooling and in the presence of a hydrolysis and condensation catalyst with the necessary quantity of water, and the resulting mixture is stirred for one to several hours. Coming into consideration as solvents are above all aliphatic alcohols, such as e.g. ethanol or i-propanol, dialkyl ketones, such as acetone or methyl isobutyl ketone, ethers, such as diethyl ether or tetrahydrofuran (THF), esters, such as ethyl or butyl acetate, and mixtures thereof.

If the hydrolytic condensation is carried out in the presence of reactive Zr, Ti or Al compounds, the addition of water should take place in stages at ca 0 to 30° C. It is usually favourable not to add water as such, but to introduce it in the form of water-containing solvents, such as aqueous ethanol, or by release via a chemical reaction, such as via an esterification.

The hydrolysis and condensation preferably takes place in the presence of a condensation catalyst, preference being given to proton- or hydroxyl ion-releasing compounds such as organic or inorganic acids or bases. Particularly preferred are volatile acids or bases, in particular hydrochloric acid or ammonia. It has proved to be worthwhile for hydrolysis and condensation to adopt procedures of sol-gel technology, as are described e.g. in C. J. Brinker et al., "Sol-Gel Science", Academic Press, Boston, 1990. The "sol-gel process" is also disclosed in DE-A-27 58 414, DE-A-27 58 415, DE-A-30 11 761, DE-A-38 26 715 and DE-A-38 35 968.

The obtained silicic acid (hetero)condensates of the silanes (I) and optionally of other hydrolytically condensable compounds can be used either as such or after partial or complete removal of the solvent used. In some cases, it can also prove to be advantageous to replace the solvent used for the hydrolytic condensation with another solvent.

The polymerizable silicic acid (hetero)condensates according to the invention and the silanes (I) and compositions containing these condensates or silanes can be cured by cationic polymerization or photopolymerization, the polymerization usually taking place after suitable initiators and other polymerizable components have been added. If different polymerizable groups, e.g. oxetane and (meth)acrylic groups, are present, several curing mechanisms, e.g. cationic and radical polymerization, can be used simultaneously or in successive stages.

Cationic initiators and/or photoinitiators are preferably used to initiate the cationic polymerization.

Preferred examples of cationic initiators are strong Brönsted and Lewis acids, e.g. sulphuric acid, trifluoroacetic acid, aluminium trichloride or boron trifluoride.

Suitable photoinitiators are onium salts, triarylsulphonium salts, diaryliodonium salts, cyclopentadienyl iron (I) salts and isoquinoline salts. Particularly suitable are a mixture of 4-(diphenylsulphino)-phenylphenylsulphide-bis-hexafluoroantimonate and bis[4-(diphenylsulphino)-phenyl] sulphide-hexafluoroantimonates (Cyraure UVI 6974, Union Carbide), bis[4-(diphenylsulphino)-phenyl]sulphide hexafluorophosphate (Degacure Kl-85, Degussa), diphenyliodonium hexafluoroantimonate or hexafluorophosphate, and the ($\eta^5$-2,4-cyclopentadien-1-yl)[1,2,3,4,5,6-$\eta$]-(cumene)-iron(I)-hexafluorophosphine complex (Irgacure 261, Ciba Geigy). The sensitivity can be increased in the visible range by sensitizers, such as thioxanthone derivatives, camphor quinone, phenanthrenequinone or perylene. Furthermore, it also proves to be advantageous to carry out the photopolymerization in the presence of radical photoinitiators, such as e.g. benzoin alkyl ethers, benzil dialkyl ketals or acrylic phosphine oxides.

In the compositions according to the invention, suitable polymerizable mono- or multifunctional monomers which are also referred to as diluent monomers can also be present in addition to the silanes (I) or the corresponding silicic acid (hetero)condensates.

Particularly suitable diluent monomers are oxetane group-containing monomers, such as 3-ethyl-3-hydroxymethyloxetane (1), 3,7-bis(3-oxetanyl)-5-oxa-nonane (3), 3,3'-(1,2-ethanediylbis(oxymethylene))-bis(3-ethyloxetane) (4), 3,3'-(1,10-decanediylbis(oxymethylene))-bis(3-ethyloxetane) (5), 3,3'-(1,3-(2-methylenyl)propanediyl-bis(oxymethylene))-bis(3-ethyloxetane) (6) or 3,3'-(1,4-xylenediylbis(oxymethylene))-bis(3-ethyloxetane) (7):

(1)

(3)

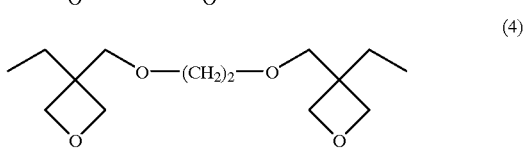

(4)

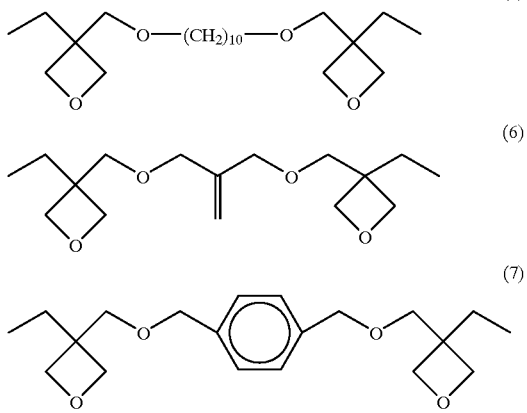

These compounds are known (cf H. Sasaki, J. V. Crivello, J. Macromol. Sci.-Pure Appl. Chem. A29 (1992) 915–930; J. V. Crivello, H. Sasaki, J. Macromol. Sci.-Pure Appl. Chem. A30 (1993) 189–206).

Moreover, radically. polymerizable diluent monomers such as monofunctional (meth)acrylates, e.g. methyl (meth) acrylate, ethyl (meth)acrylate, butyl (meth)acrylate, benzyl (meth)acrylate, furfuryl (meth)acrylate or phenyl (meth) acrylate, and polyfunctional (meth)acrylates, e.g. bisphenyl-A-di(meth)acrylate, bis-GMA (an addition product of methacrylic acid and bisphenol-A-diglycidyl ether), UDMA (an addition product of 2-hydroxyethyl methacrylate and 2,2,4-hexamethylene diisocyanate), di-, tri- or tetraethylene glycol di(meth)acrylate, decanediol di(meth)acrylate, trimethylolpropane tri(meth)acrylate, pentaerythritol tetra(meth) acrylate, butanediol di(meth)acrylate, 1,10-decanediol di(meth)acrylate or 1,12-dodecanediol di(meth)acrylate, can also be used.

The silanes according to the invention, the silicic acid condensates or silicic acid heterocondensates thereof and compositions containing them can be used as such or in at least partially polymerized form as varnishes for coating plastics, glass or other substrates, as fillers or bulk material for composites and for producing medical materials such as contact lenses. They are, however, particularly preferably used as dental material or a constituent thereof.

The compositions according to the invention can also optionally contain other additives, such as e.g. coloring agents (pigments or dyes), stabilizers, flavorants, microbiocidal active ingredients, flameproofing agents, plasticizers or UV absorbers.

Other preferred additives are fillers. Examples of preferred fillers are quartz, glass ceramic or glass powders, in particular barium or strontium silicate glass powder, lithium-aluminium silicate glass powder, silicon, zirconium or aluminium oxides, or mixtures thereof, finely divided silicas, in particular pyrogenic or precipitated silicas, and X-ray-opaque fillers, such as e.g. ytterbium trifluoride.

A particularly preferred composition according to the invention contains:
  (a) 5 to 90, in particular 10 to 70 wt. %, relative to the composition, of silicic acid (hetero)condensate of a silane (I),
  (b) 0 to 80, in particular 0 to 50 wt. %, relative to the composition, of diluent monomer,
  (c) 0.1 to 5, in particular 0.2 to 2.0 wt. %, relative to the composition, of polymerization initiator, and/or
  (d) 0 to 90, in particular 0 to 80 wt. %, relative to the composition, of fillers.

The compositions according to the invention are particularly preferably used as dental cement, dental filling material or dental bonding for filling materials. The compositions are used in particular by applying them to the area of a false or natural tooth to be treated and curing by polymerization.

It proves to be a particular advantage of the compositions according to the invention that on the one hand they exhibit only a low polymerization shrinkage and on the other hand the, result in composite materials with high mechanical strength. Such a combination of properties is of particular significance especially in the case of dental materials.

The invention is explained in more detail below with reference to examples.

EXAMPLE 1

Synthesis of 7-trimethoxysilyl-4-thia-heptanoic acid-(3-ethyloxetan-3-yl) methyl ester (8)

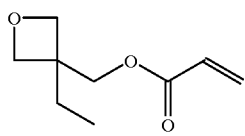

1st Stage: 3-ethyloxetan-3-yl-methyl acrylate 62.3 g (688 mmol) of acrylic acid chloride in 300 ml of diethyl ether were added dropwise to an ice-cooled solution of 80 g (688 mmol) of 3-ethyl-3-hydroxyethyl-oxetane and 77.3 g of collidine (688 mmol) in 400 ml of diethyl ether. After 6 hrs' stirring at room temperature, the formed hydrochloride was filtered off, and the filtrate was washed with aqueous hydrochloric acid and with $NaHCO_3$ solution. After drying with anhydrous $Na_2SO_4$ and additional stabilizing with hydroquinone monomethyl ether, the solvent was drawn off at 120 mbar in a rotary evaporator. After fractional distillation (b.p.$_{0.2}$:56° C.), 57 g (50% yield) of a colourless, clear liquid were obtained.

$^1$H-NMR: 5.6–6.6 (m, 3H, CH=$CH_2$), 3.4–4.7 (m, 6H, $CH_2O$), 1.6–1.9 (q, 2H, $CH_2$), 0.7–1.0 (t, 3H, $CH_3$) ppm. IR (Film): 2965, 2874, 1728, 1408, 1268, 1194 cm$^{-1}$.

2nd Stage: 7-trimethoxysilyl-4-thia-heptanoic acid-(3-ethyloxetan-3-yl)methyl ester)

(8)

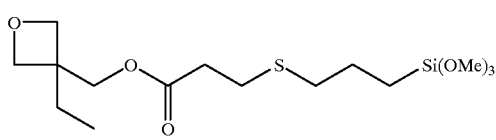

17.0 g (0.1 mol) of 3-ethyl-oxetan-3-yl-methyl acrylate were added in a dry and argon-flushed apparatus to 19.6 g (0.1 mol) of 3-mercaptopropyl-trimethoxy-silane, and the whole was stirred for 48 hrs at room temperature. After all volatile constituents had been removed by drying at 60° C. at 0.1 mbar, 30 g (81% yield) of a colourless liquid were obtained.

$^1$H-NMR: 4.2–4.5 (m, 6H, $CH_2O$), 3.6 (s, 9H, $CH_3O$), 2.3–2.9 (m, 6H, $CH_2S$, $CH_2C$=O), 1.6–1.0 (m, 4H, $CH_2$), 0.8–1.0 (t, 3H, $CH_3$), 0.6–0.7 (t, 2H, $CH_2Si$) ppm. IR (Film): 2940, 2870, 1737, 1459, 1244, 1089 cm$^{-1}$.

EXAMPLE 2

Synthesis of N-(3-triethoxysilylpropyl)-(3-ethyloxetan-3-yl)-methyl carbamate (9)

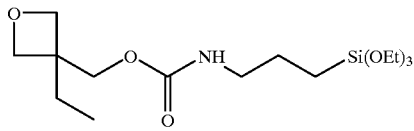

(9)

11.6 g (0.1 mol) of 3-(3-ethyloxetanyl)methanol were added under argon in a dry apparatus to 24.7 g (0.1 mol) of 3-isocyanatopropyl triethoxysilane and 25 ml of anhydrous ether. After 20 mg of dibutyltin dilaurate had been added, the mixture was stirred for 6 hrs at room temperature. After the solvent had been drawn off, 30 g (ca 85%) of a colourless liquid remained.

Elemental analysis:

| $C_{16}H_{33}NO_6Si$ [363.5] | Calc.: C 52.86 | H 9.15 | N 3.85 |
|---|---|---|---|
| | Found: C 51.52 | H 9.48 | N 3.76 |
| $^1$H-NMR: | 5.6(br, H, NH), 4.4–4.5(q, 4H, $CH_2O$), 4.2(s, 2H, $CH_2O$), 3.6–3.8(q, 6H$CH_2O$), 3.0–3.3(q, 2H, $CH_2N$), 1.4–1.8(m, 4H, $CH_2$), 1.1–1.3(t, 9H, $CH_3$), 0.9(t, 3H, $CH_3$), 0.4–0.7(t, 2H, $CH_2Si$)ppm. | | |
| IR (Film): | 3336, 2972, 2930, 2880, 1724, 1533, 1245, 1080 cm$^{-1}$. | | |

EXAMPLE 3

Synthesis of 2-(3-triethoxysilylpropylthio) succinic acid-bis-[(3-ethyloxetan-3-yl)-methyl]ester (10)

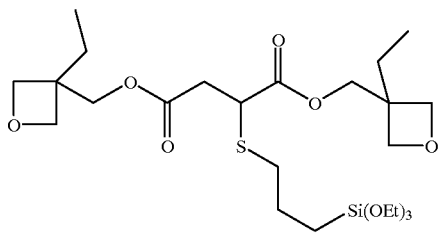

(10)

8.4 g (26.9 mmol) of fumaric acid-bis-[(3-ethyloxetan-3-yl)methyl]ester, 5.3 g (26.9 mmol) of 3-mercaptopropyltriethoxysilane and 0.33 g (1.3 mmol) of dibenzoyl peroxide were stirred for 5 hours in 20 ml of toluene at 100° C. When the solvent was distilled off, a white deposit precipitated which produced 10.2 g (70% yield) of (10) after filtering off and drying.

EXAMPLE 4

Preparation of a Silicic Acid Condensate Based on Silane (8)

20 mmol of silane (8) and 20 mmol of dimethyldimethoxysilane were dissolved in 50 ml of anhydrous ethanol. After a mixture of 50 mmol of water and 5 ml of ethanol and some drops of 0.1 molar ethanolic acetic acid solution had been added, the whole was heated under reflux for 5 hours and was stirred overnight. After removal of volatile components in vacuo, the formed resin (7 g) could be used for a cationic polymerization.

EXAMPLE 5

Preparation of a Dental Bonding 70 mg, i.e. 1 wt. %, of Cyraure UVI 6974 (Union Carbide) were added to a mixture of 4 g of resin from Example 4 and 3 g of 3,7-bis(3-oxetanyl)-5-oxanonane (3). The mixture was then cast as a film and irradiated for 60 s in a dental irradiation device, namely Heliomat (Vivadent). A solid, well adhering film formed. The densities of the starting resin and the polymerisate were determined in each case according to the buoyancy method, the change in volume, i.e. the shrinkage, during the cationic ring-opening polymerisation being given by the density difference. The obtained $\Delta V$ value of only −4.1% was clearly lower than that for conventional bondings based on methacrylate. For example, the volume shrinkage during the curing of the commercially available bonding Heliobond (Vivadent) is 7.5%.

What is claimed is:

1. A dental material comprising a polymer of an oxetane silane of the general formula (I) and stereoisomers thereof

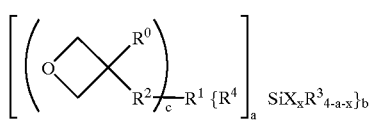

(I)

in which the variables $R^0$, $R^1$, $R^2$, $R^3$, $R^4$, $R^5$, $R^6$, X, Y, a, b, c, and x, unless otherwise stated, independently of one another have the following meanings:

$R^0$=hydrogen or substituted or unsubstituted $C_1$ to $C_{10}$ alkyl;

$R^1$=missing or represents substituted or unsubstituted $C_1$ to $C_{18}$ alkylene, $C_6$ to $C_{18}$ arylene, $C_7$ to $C_{18}$ alkylenearylene, or arylenealkylene, these radicals being able to be interrupted by at least one group selected from the group consisting of ether, thioether, ester, carbonyl, amide, and urethane groups;

$R^2$=missing or represents substituted or unsubstitituted $C_1$ to $C_{18}$ alkylene, $C_6$ to $C_{18}$ arylene, $C_7$ to $C_{18}$ alkylenearylene, or $C_7$ to $C_{18}$ arylenealkylene, these radicals being able to be interrupted by at least one group selected from the group consisting of ether, thioether, ester, thioester, carbonyl, amide, and urethane groups or being able to bear these in the terminal position;

$R^3$=missing or represents substituted or unsubstitituted $C_1$ to $C_{18}$ alkyl, $C_2$ to $C_{18}$ alkenyl, $C_6$ to $C_{18}$ aryl, $C_7$ to $C_{18}$ alkylaryl, or $C_7$ to $C_{18}$ arylalkyl, these radicals being able to be interrupted by at least one group selected from the group consisting of ether, thioether, ester, carbonyl, amide, and urethane groups;

$R^4$=missing or represents substituted or unsubstituted —$CHR^6$—$CHR^6$, —$CHR^6$—$CHR^6$—S—$R^5$—, —S—$R^5$—, —Y—CO—NH—$R^5$—, or —CO—O—$R^5$—;

$R^5$=substituted or unsubstitituted $C_1$ to $C_{18}$ alkylene, $C_6$ to $C_{18}$ arylene, $C_6$ to $C_{18}$ alkylenearylene, or $C_6$ to $C_{18}$ arylenealkylene, these radicals being able to be interrupted by at least one group selected from the group consisting of ether, thioether, ester, carbonyl, amide, and urethane groups;

$R^6$=hydrogen or substituted or unsubstituted $C_1$ to $C_{18}$ alkyl or $C_6$ to $C_{10}$ aryl;

X=a hydrolysable group, namely halogen, hydroxy, alkoxy, or acyloxy;

Y=O or S;

a=1, 2, or 3;

b=1, 2, or 3;

c=1 or 2; and x=1, 2, or 3;

and with the proviso that
(i) a+x=2, 3, or 4 and
(ii) a and/or b 1.

2. A dental material comprising a polymerizable silicic acid condensate of a hydrolysable and polymerizable oxetane silane of the general formula (I) and stereoisomers thereof

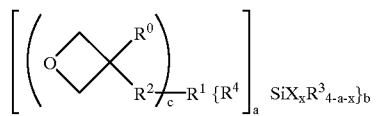
(I)

in which the variables $R^0$, $R^1$, $R^2$, $R^3$, $R^4$, $R^5$, $R^{,6}$, X, Y, a, b, c, and x, unless otherwise stated, independently of one another have the following meanings:

$R^0$=hydrogen or substituted or unsubstituted $C_1$ to $C_{10}$ alkyl;

$R^1$=missing or represents substituted or unsubstituted $C_1$ to $C_{18}$ alkylene, $C_6$ to $C_{18}$ arylene, $C_7$ to $C_{18}$ alkylenearylene, or arylenealkylene, these radicals being able to be interrupted by at least one group selected from the group consisting of ether, thioether, ester, carbonyl, amide, and urethane groups;

$R^2$=missing or represents substituted or unsubstitituted $C_1$ to $C_{18}$ alkylene, $C_6$ to $C_{18}$ arylene, $C_7$ to $C_{18}$ alkylenearylene, or $C_7$ to $C_{18}$ arylenealkylene, these radicals being able to be interrupted by at least one group selected from the group consisting of ether, thioether, ester, thioester, carbonyl, amide, and urethane groups or being able to bear these in the terminal position;

$R^3$=missing or represents substituted or unsubstitituted $C_1$ to $C_{18}$ alkyl, $C_2$ to $C_{18}$ alkenyl, $C_6$ to $C_{18}$ aryl, $C_7$ to $C_{18}$ alkylaryl, or $C_7$ to $C_{18}$ arylalkyl, these radicals being able to be interrupted by at least one group selected from the group consisting of ether, thioether, ester, carbonyl, amide, and urethane groups;

$R^4$=missing or represents substituted or unsubstituted —$CHR^6$—$CHR^6$—, —$CHR^6$—$CHR^6$—S—$R^5$—, —S—$R^5$—, —Y—CO—NH—$R^5$—, or —CO—O—$R^5$—;

$R^5$=substituted or unsubstitituted $C_1$ to $C_{18}$ alkylene, $C_6$ to $C_{18}$ arylene, $C_6$ to $C_{18}$ alkylenearylene, or $C_6$ to $C_{18}$ arylenealkylene, these radicals being able to be interrupted by at least one group selected from the group consisting of ether, thioether, ester, carbonyl, amide, and urethane groups;

$R^6$=hydrogen or substituted or unsubstituted $C_1$ to $C_{18}$ alkyl or $C_6$ to $C_{10}$ aryl;

X=a hydrolysable group, namely halogen, hydroxy, alkoxy, or acyloxy;

Y=O or S;

a=1, 2, or 3;

b=1, 2, or 3;

c=1 or 2; and x=1, 2, or 3;

and with the proviso that
(i) a+x=2, 3, or 4 and
(ii) a and/or b=1.

3. A dental material comprising a polymer of the silicic acid condensate according to claim 2.

4. A method of producing a dental material comprising:

providing a hydrolysable and polymerizable oxetane silane of the general formula (I) and stereoisomers thereof

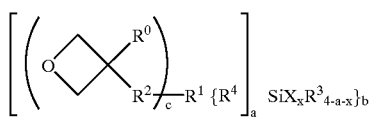
(I)

in which the variables $R^0$, $R^1$, $R^2$, $R^3$, $R^4$, $R^5$, $R^6$, X, Y, a, b, c, and x, unless otherwise stated, independently of one another have the following meanings:

$R^0$=hydrogen or substituted or unsubstituted $C_1$ to $C_{10}$ alkyl;

$R^1$=missing or represents substituted or unsubstituted $C_1$ to $C_{18}$ alkylene, $C_6$ to $C_{18}$ arylene, $C_7$ to $C_{18}$ alkylenearylene, or arylenealkylene, these radicals being able to be interrupted by at least one group selected from the group consisting of ether, thioether, ester, carbonyl, amide, and urethane groups;

$R^2$=missing or represents substituted or unsubstitituted $C_1$ to $C_{18}$ alkylene, $C_6$ to $C_{18}$ arylene, $C_7$ to $C_{18}$ alkylenearylene, or $C_7$ to $C_{18}$ arylenealkylene, these radicals being able to be interrupted by at least one group selected from the group consisting of ether, thioether, ester, thioester, carbonyl, amide, and urethane groups or being able to bear these in the terminal position;

$R^3$=missing or represents substituted or unsubstitituted $C_1$ to $C_{18}$ alkyl, $C_2$ to $C_{18}$ alkenyl, $C_6$ to $C_{18}$ aryl, $C_7$ to $C_{18}$ alkylaryl, or $C_7$ to $C_{18}$ arylalkyl, these radicals being able to be interrupted by at least one group selected from the group consisting of ether, thioether, ester, carbonyl, amide, and urethane groups;

$R^4$=missing or represents substituted or unsubstituted —$CHR^6$—$CHR^6$—, —$CHR^6$—$CHR^6$—S—$R^5$—, —S—$R^5$—, —Y—CO—NH—$R^5$—, or —CO—O—$R^5$—;

$R^5$=substituted or unsubstitituted $C_1$ to $C_{18}$ alkylene, $C_6$ to $C_{18}$ arylene, $C_6$ to $C_{18}$ alkylenearylene, or $C_6$ to $C_{18}$ arylenealkylene, these radicals being able to be interrupted by at least one group selected from the group consisting of ether, thioether, ester, carbonyl, amide, and urethane groups;

$R^6$=hydrogen or substituted or unsubstituted $C_1$ to $C_{18}$ alkyl or $C_6$ to $C_{10}$ aryl;

X=a hydrolysable group, namely halogen, hydroxy, alkoxy, or acyloxy;

Y=O or S;

a=1, 2, or 3;

b=1, 2, or 3;

c=1 or 2; and x=1, 2, or 3;
and with the proviso that
(i) a+x=2, 3, or 4 and
(ii) a and/or b=1 and
polymerizing the oxetane silane under conditions effective to produce the dental material.

5. A method of producing a dental material comprising:
providing a polymerizable silicic acid condensate of a hydrolysable and polymerizable oxetane silane of the general formula (I) and stereoisomers thereof

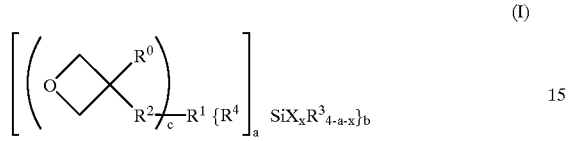

(I)

in which the variables $R^0$, $R^1$, $R^2$, $R^3$, $R^4$, $R^5$, $R^6$, X, Y, a, b, c, and x, unless otherwise stated, independently of one another have the following meanings:

$R^0$=hydrogen or substituted or unsubstituted $C_1$ to $C_{10}$ alkyl;

$R^1$=missing or represents substituted or unsubstituted $C_1$ to $C_{18}$ alkylene, $C_6$ to $C_{18}$ arylene, $C_7$ to $C_{18}$ alkylenearylene, or arylenealkylene, these radicals being able to be interrupted by at least one group selected from the group consisting of ether, thioether, ester, carbonyl, amide, and urethane groups;

$R^2$=missing or represents substituted or unsubstituted $C_1$ to $C_{18}$ alkylene, $C_6$ to $C_{18}$ arylene, $C_7$ to $C_{18}$ alkylenearylene, or $C_7$ to $C_{18}$ arylenealkylene, these radicals being able to be interrupted by at least one group selected from the group consisting of ether, thioether, ester, thioester, carbonyl, amide, and urethane groups or being able to bear these in the terminal position;

$R^3$=missing or represents substituted or unsubstitituted $C_1$ to $C_{18}$ alkyl, $C_2$ to $C_{18}$ alkenyl, $C_6$ to $C_{18}$ aryl, $C_7$ to $C_{18}$ alkylaryl, or $C_7$ to $C_{18}$ arylalkyl, these radicals being able to be interrupted by at least one group selected from the group consisting of ether, thioether, ester, carbonyl, amide, and urethane groups;

$R^4$=missing or represents substituted or unsubstituted —$CHR^6$—$CHR^6$—, —$CHR^6$—$CHR^6$—S—$R^5$—, —S—$R^5$—, —Y—CO—NH—$R^5$—, or —CO—O—$R^5$—;

$R^5$=substituted or unsubstitituted $C_1$ to $C_{18}$ alkylene, $C_6$ to $C_{18}$ arylene, $C_6$ to $C_{18}$ alkylenearylene, or $C_6$ to $C_{18}$ arylenealkylene, these radicals being able to be interrupted by at least one group selected from the group consisting of ether, thioether, ester, carbonyl, amide, and urethane groups;

$R^6$=hydrogen or substituted or unsubstituted $C_1$ to $C_{18}$ alkyl or $C_6$ to $C_{10}$ aryl;

X=a hydrolysable group, namely halogen, hydroxy, alkoxy, or acyloxy;

Y=O or S;

a=1, 2, or 3;

b=1, 2, or 3;

c=1 or 2; and x=1, 2, or 3;

and with the proviso that
(i) a+x=2, 3, or 4 and
(ii) a and/or b=1 and
polymerizing the silicic acid condensate under conditions effective to produce the dental material.

* * * * *